United States Patent
Yoshida et al.

[11] Patent Number: 5,874,605
[45] Date of Patent: Feb. 23, 1999

[54] PROCESS FOR PREPARING AROMATIC CARBONIC ESTER

[75] Inventors: Hiroshi Yoshida, Suita; Hideaki Tsuneki, Shinagawa-ku; Atusi Moriya, Suita; Hiroki Wakayama, Suita; Kenichi Watanabe, Suita; Yoshiyuki Onda, Suita, all of Japan

[73] Assignee: Nippon Shokubai Co., Ltd., Osaka, Japan

[21] Appl. No.: 465
[22] PCT Filed: Jun. 10, 1997
[86] PCT No.: PCT/JP97/02000
  § 371 Date: Feb. 3, 1998
  § 102(e) Date: Feb. 3, 1998
[87] PCT Pub. No.: WO97/47586
  PCT Pub. Date: Dec. 18, 1997

[30] Foreign Application Priority Data

Jun. 14, 1996 [JP] Japan ................................. 8-154542

[51] Int. Cl.⁶ .................................................. C07C 68/06
[52] U.S. Cl. ............................................................ 558/274
[58] Field of Search ............................................. 558/274

[56] References Cited

U.S. PATENT DOCUMENTS 4,533,504  8/1985  Bolon et al.
5,210,268  5/1993  Fukuoka et al. ................. 558/274 X
5,543,546  8/1996  Tsuneki et al. .................. 558/274 X

FOREIGN PATENT DOCUMENTS 56-123948   9/1981  Japan.
3-291257   12/1991  Japan.
4-9358      1/1992  Japan.
7-304713   11/1995  Japan.
8-73412     3/1996  Japan.

Primary Examiner—Michael G. Ambrose
Attorney, Agent, or Firm—Nixon & Vanderhye P.C.

[57] ABSTRACT

An aromatic carbonate ester is continuously and efficiently prepared by the transesterification of an aromatic carboxylate with an aliphatic carbonate ester and/or aromatic.aliphatic carbonate ester. A raw material including an aromatic carboxylate, aliphatic carbonate ester and/or aromatic.aliphatic carbonate ester, and a catalyst are continuously fed to a first stage of a reactive distillation column (1) through a raw material feeding pipe (5). Meanwhile, an aliphatic carbonate ester (a) whose boiling point is lower than that of a reactant liquid that is present in a second stage lower than the first stage is continuously fed to the second stage through an aliphatic carbonate ester (a) feeding pipe (6). The second stage is preferably a column bottom section of the reactive distillation column (1). The amount of aliphatic carbonate ester (a) fed is preferably 0.001 to 5 times, by weight, more than the amount of the raw material fed.

8 Claims, 2 Drawing Sheets ated esters, many methods have been proposed. For example,
PROCESS FOR PREPARING AROMATIC CARBONIC ESTER

TECHNICAL FIELD

The present invention relates to a process for preparing an aromatic carbonate ester by transesterification of an aromatic carboxylate with an aliphatic carbonate ester and/or aromatic.aliphatic carbonate ester using a multistage reactive distillation equipment. The aromatic carbonate esters are industrially useful compounds.

BACKGROUND ART

As a process for preparing an aromatic carbonate ester by, for example, transesterification of an aliphatic carbonate ester with an aromatic hydroxy compound or aromatic carboxylate has been known. In particular, as a process for preparing diphenyl carbonate as a kind of aromatic carbonate esters, many methods have been proposed. For example, U.S. Pat. No. 4,533,504 discloses a process for preparing diphenyl carbonate by reacting dimethyl carbonate as a kind of aliphatic carbonate esters with phenyl acetate as a kind of aromatic carboxylates.

Moreover, Japanese Patent Publication (Tokukaihei) No. 3-291257 discloses a process for preparing a diphenyl carbonate as a target product using a continuous multistage distillation column (reactive distillation equipment) in which a reaction of dimethyl carbonate with phenol as a kind of aromatic hydroxy compounds is carried out to generate methyl phenyl carbonate, and then methyl phenyl carbonate is disproportionated to produce diphenyl carbonate.

In the method disclosed in U.S. Pat. No. 4,533,504, the conversion of dimethyl carbonate is as high as 70 mole percent or more. However, since this method is a batch system, high productivity cannot be achieved. Therefore, diphenyl carbonate can not be prepared efficiently by this method.

The method disclosed in Japanese Patent Publication (Tokukaihei) No. 3-291257 also suffers from low productivity because the conversion of dimethyl carbonate is around 1.6 mole percent to 24 mole percent. Additionally, in this method, since diphenyl carbonate is obtained by disproportionation of methyl phenyl carbonate, many processing steps need to be carried out to prepare the diphenyl carbonate. Thus, the diphenyl carbonate cannot be prepared efficiently by this method.

Therefore, there is a great demand for a process that ensures efficient preparation of diphenyl carbonate, i.e., aromatic carbonate ester. Namely, in order to solve the above-mentioned problems associated with the conventional methods, it is an object of the present invention to provide a process for continuously and efficiently preparing aromatic carbonate esters.

DISCLOSURE OF THE INVENTION

In order to solve the problems associated with the conventional methods, the present inventors eagerly studied the process for preparing aromatic carbonate esters. The inventors found as a result of study that the reaction efficiency of the transesterification of an aromatic carboxylate with an aliphatic carbonate ester and/or aromatic.aliphatic carbonate ester using a multistage reactive distillation equipment can be improved by continuously feeding a raw material including these compounds to the first stage of the equipment and continuously feeding to the second stage lower than the first stage an aliphatic carbonate ester whose boiling point is lower than that of a reactant liquid that is present in the second stage. In short, the inventors completed the present invention based on such a discovery that the aromatic carbonate ester can be continuously and efficiently prepared by feeding the aliphatic carbonate ester whose boiling point is lower than the boiling point of the reactant liquid that is present in the second stage continuously to the second stage lower than the first stage to which the raw material is fed.

Namely, in order to solve the above-mentioned problems, a process for preparing aromatic carbonate esters of the present invention is a process for preparing an aromatic carbonate ester by transesterification of an aromatic carboxylate with an aliphatic carbonate ester and/or aromatic.aliphatic carbonate ester, and characterized by using a multistage reactive distillation equipment having a first stage and a second stage lower than the first stage, and feeding a raw material including the aromatic carboxylate and the aliphatic carbonate ester and/or aromatic.aliphatic carbonate ester continuously to the first stage while feeding the aliphatic carbonate ester whose boiling point is lower than that of a reactant liquid that is present in the second stage continuously to the second stage.

In general, the multistage reactive distillation equipment has a heat source at the bottom of a column. Therefore, the temperature gradually decreases from the bottom toward the top of the column, and the boiling point of the reactant liquid in each stage becomes lower gradually from the bottom toward the top of the column.

In this method, therefore, by feeding an aliphatic carbonate ester whose boiling point is lower than that of the reactant liquid flowing downward to the second stage continuously to the second stage lower than the first stage to which the raw material is continuously fed, at least a portion of the aliphatic carbonate ester having the lower boiling point vaporizes in the second stage, resulting in a lowering of the boiling point.

Hence, in the above-mentioned method, by maintaining the boiling point at the second stage, the operation pressure in the column of the reactive distillation equipment can be increased, and the boiling point at the upper part of the reactive distillation equipment increases. It is therefore possible to retain the reaction temperature in the upper part at a high value. As a result, the reaction rate of the multistage reactive distillation equipment as a whole increases, thereby improving the efficiency of the preparation of aromatic carbonate esters in the reactive distillation equipment.

Consequently, in the above-mentioned method, by feeding an aliphatic carbonate ester whose boiling point is lower than that of the reactant liquid that is present in the second stage lower than the first stage continuously to the second state, it is possible to continuously and efficiently prepare aromatic carbonate esters in the multistage reactive distillation equipment.

In this method, it is preferred that the second stage is the column bottom section of the reactive distillation equipment. It is also preferred that the amount of aliphatic carbonate ester fed to the second stage is 0.001 to 5 times, by weight, more than the amount of the raw material fed.

With the use of either the above-mentioned methods, it is possible to prepare aromatic carbonate esters continuously and more efficiently.

BEST MODE FOR IMPLEMENTING THE INVENTION

Figure 1:
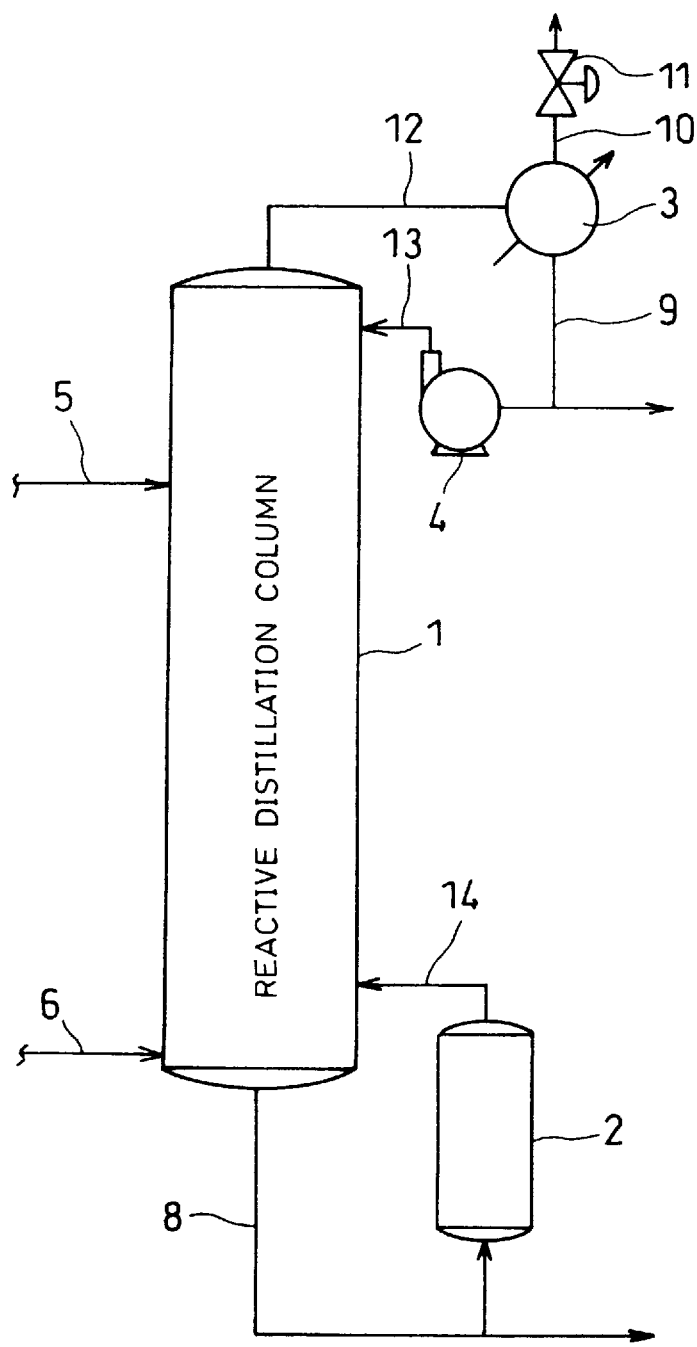
FIG. 1 is a block diagram showing a schematic structure of a reactive distillation equipment suitable for use with a preparation process according to an embodiment of the present invention.

The following description will explain one embodiment of the present invention with reference to FIG. 1. In this invention, "the boiling point of the reactant liquid" means the boiling point of a mixed liquid containing a plurality of components composing the reactant liquid. In this invention, the "column bottom section" means the bottom of column of the reactive distillation equipment, and includes up to about the (⅕)nth stage from the bottom, n being the number of the whole stages in the reactive distillation equipment.

Moreover, in the present invention, aliphatic carbonate esters denote carbonate esters having two aliphatic groups as substituents. Aromatic.aliphatic carbonate esters are carbonate esters having an aliphatic group and an aromatic group as substituents. Aromatic carbonate esters mean carbonate esters having two aromatic groups as substituents.

A process for preparing aromatic carbonate esters according to the present invention is a method of preparing an aromatic carbonate ester by carrying out transesterification of an aromatic carboxylate with aliphatic carbonate ester and/or aromatic.aliphatic carbonate ester using a multistage reactive distillation equipment by continuously feeding a raw material including the aromatic carboxylate and the aliphatic carbonate ester and/or aromatic.aliphatic carbonate ester (hereinafter just referred to as the raw material) to the first stage of the reactive distillation equipment while feeding an aliphatic carbonate ester whose boiling point is lower than a reactant liquid that is present in the second stage lower than the first stage continuously to the second stage.

In the case where there is a necessity to distinguish the aliphatic carbonate ester contained in the raw material from the aliphatic carbonate ester to be fed to the second stage, the aliphatic carbonate ester to be fed to the second stage will be referred to as aliphatic carbonate ester (a) for the sake of convenience of explanation.

Specific examples of the aromatic carboxylate include: phenyl acetate, isomers of methyl phenyl acetate, isomers of ethyl phenyl acetate, isomers of chlorophenyl acetate, isomers of isopropylphenyl acetate, isomers of methoxyphenyl acetate, isomers of dimethyl phenyl acetate, isomers of naphthyl acetate, phenyl propionate, isomers of methyl phenyl propionate, phenyl butyrate, phenyl isobutyrate, phenyl valerate, isomers of methyl phenyl valerate, phenyl isovalerate, phenyl hexanoate, and phenyl heptanoate. However, the aromatic carboxylate is not necessarily limited to these compounds.

In the transesterification of the aromatic carboxylate with the aliphatic carbonate ester and/or aromatic.aliphatic carbonate ester, in order to increase the reaction efficiency (equilibrium conversion) by biasing the equilibrium of the transesterification toward the product system, an aliphatic carboxylate to be by-produced is continuously removed from the reaction system. Therefore, among the above-listed compounds, an aromatic carboxylate having a boiling point higher than that of the aliphatic carboxylate is more preferred.

Specific examples of the aliphatic carbonate ester include: dimethyl carbonate, diethyl carbonate, di-n-propyl carbonate, diisopropyl carbonate, isomers of dibutyl carbonate, isomers of dipentyl carbonate, isomers of dihexyl carbonate, isomers of diheptyl carbonate, isomers of dioctyl carbonate, isomers of dinonyl carbonate, isomers of didecyl carbonate, dicyclohexyl carbonate, dibenzyl carbonate, isomers of diphenethyl carbonate, and isomers of di(methylbenzyl) carbonate. The aliphatic carbonate ester is not necessarily limited to these compounds. These aliphatic carbonate esters can be suitably mixed for use. Among the listed compounds, dimethyl carbonate is suitable for industrial use.

As the aliphatic carbonate ester (a), for example, the above-listed aliphatic carbonate esters can be used. Among these compounds, dimethyl carbonate is suitable for industrial use.

Examples of the aromatic.aliphatic carbonate ester are carbonate esters produced by substituting one of the two aliphatic groups of the above-listed aliphatic carbonate esters with an aromatic group. However, the aromatic.aliphatic carbonate ester is not particularly limited to these compounds. Specific examples of the aromatic groups are aromatic groups that the above-listed aromatic carboxylates have. These aromatic.aliphatic carbonate esters can be suitably mixed for use. In the case of using both of the aliphatic carbonate ester and aromatic.aliphatic carbonate ester, the ratio thereof is not particularly limited.

In order to continuously remove the aliphatic carboxylate from the reaction system, it is preferred to use an aromatic.aliphatic carbonate ester whose boiling point is higher than that of the aliphatic carboxylate. Moreover, in order to continuously remove the aromatic carbonate ester to be produced from the reaction system, it is preferred to use an aromatic carboxylate, aliphatic carbonate ester, and aromatic.aliphatic carbonate ester whose boiling points are lower than that of the aromatic carbonate ester.

Furthermore, in order to facilitate the separation of the aromatic carbonate ester to be produced and the aromatic carboxylate, it is preferred that there is a relatively large difference in boiling point between these compounds. Additionally, in order to improve the equilibrium conversion of the aliphatic carbonate ester and the aromatic.aliphatic carbonate ester, it is preferred that the difference in boiling point between the raw materials, i.e., the aromatic carboxylate and the aliphatic carbonate ester and aromatic.aliphatic carbonate ester, is relatively small and that the difference in boiling point between the aromatic carboxylate and the aliphatic carboxylate is relatively large, i.e., larger than the difference in boiling point between the raw materials.

Although the mole ratio of the aromatic carboxylate to the aliphatic carbonate ester and/or the aromatic.aliphatic carbonate ester varies depending on the kind and amount of a catalyst to be used (described later) or the reaction conditions, it is preferably in a range of from 1:100 to 100:1, more preferably in a range of 1:20 to 20:1, and most preferably in a range of from 1:10 to 10:1. The aliphatic carbonate ester to be fed as the aliphatic carbonate ester (a) is included in calculating the mole ratio.

The aromatic carboxylate may include a raw material for preparing the aromatic carboxylate, i.e., unreacted compounds. Examples of the unreacted compounds include aliphatic carboxylates, and aromatic hydroxy compounds. However, when the unreacted compound is mixed into the aromatic carboxylate, the content of the aromatic carboxylate in the mixture is preferably not less than 10 mole percent, and more preferably not less than 20 mole percent in order to efficiently prepare the aromatic carbonate ester.

The amount of the aliphatic carbonate ester (a) fed is preferably 0.001 to 5 times, by weight, more than the amount of the raw material fed, and more preferably 0.01 to 1 times, by weight, more than the amount of the raw material fed. When the amount of the aliphatic carbonate ester (a) fed is less than an amount that is 0.001 times, by weight, more than the amount of the raw material fed, the effect produced by the feeding of the aliphatic carbonate ester (a) is diminished, causing an unsatisfactory result. On the other hand, when the amount of the aliphatic carbonate ester (a) fed exceeds an amount that is 5 times, by weight, more than the amount of the raw material fed, the aliphatic carbonate ester (a) becomes excessive, resulting in a lowering of the productivity and an increase in the cost of utility for collecting the aliphatic carbonate ester (a).

When the aliphatic carbonate ester is used, the transesterification is carried out by two steps of reactions, namely, a reaction for producing the aromatic.aliphatic carbonate ester, and a reaction for producing the aromatic carbonate ester.

As illustrated in FIG. 1, a reactive distillation equipment, which is suitably used with the preparation process, includes a reactive distillation column 1, a reboiler 2, condenser 3, a pump 4, a pressure regulating valve 11, etc.

The reactive distillation column 1 needs to have a vapor phase section therein so that a low-boiling point component produced is continuously separated, removed and guided to the vapor phase section, i.e., a structure capable of carrying out a so-called reactive distillation.

As the reactive distillation column 1, a continuous multistage distillation column having not less than two states in addition to the top stage and bottom stage is suitable. For such a distillation column, it is possible to employ generally-used distillation columns, for example, packed columns packed with various packings, such as Raschig ring, Pall ring, Intelox saddle, Dixon packing, McMahon packing, and Sulzer packing; and plate columns using trays (plates), such as a bubble cap tray, sieve tray, and valve tray. It is also possible to use a composite distillation column having both plates and a packing bed. The number of stages means the number of plates in a plate column or the number of theoretical stages in a packed column.

The reactive distillation column 1 is a vapor-liquid contact type reactor for carrying out vapor-liquid contacting between the aromatic carboxylate and the aliphatic carbonate ester and/or aromatic.aliphatic carbonate ester. The reactive distillation column 1 is connected to a raw material feeding pipe 5, and an aliphatic carbonate ester (a) feeding pipe 6. The reboiler 2 is connected to the bottom of the reactive distillation column 1 through an extracting pipe 8 and a conduit 14. The condenser 3 is connected to the top of the reactive distillation column 1 through a conduit 12.

The raw material feeding pipe 5 and aliphatic carbonate ester (a) feeding pipe 6 are disposed on different stages. More specifically, the raw material feeding pipe 5 is connected to a first stage that is not the lowest stage, and the aliphatic carbonate ester (a) feeding pipe 6 is connected to a second stage lower than the first stage.

The aliphatic carbonate ester (a) feeding pipe 5 is connected preferably to the column bottom section, and more preferably to the bottom of the reactive distillation column 1. As the first stage to which the raw material feeding pipe 5 is connected, the middle stage or a stage near the middle stage of the reactive distillation column 1 is suitable. However, the first stage is not necessarily limited to these stages.

The raw material feeding pipe 5 continuously feeds the raw material to the reactive distillation column 1. The aliphatic carbonate ester (a) feeding pipe 6 continuously feeds the aliphatic carbonate ester (a) to the reactive distillation column 1.

The aliphatic carbonate ester (a) fed to the reactive distillation column 1 through the aliphatic carbonate ester (a) feeding pipe 6 needs to be a compound whose boiling point is lower than the boiling point of the reactant liquid in the second stage. Although this compound is not particularly limited, it is preferably the aliphatic carbonate ester included in the raw material. When the aliphatic carbonate ester included in the raw material is used, it is possible to eliminate the step of collecting the aliphatic carbonate ester (a), if necessary. Thus, the use of the aliphatic carbonate ester included in the raw material is industrially advantageous.

The reboiler 2 is connected to the bottom of the reactive distillation column 1 through the extracting pipe 8 and the conduit 14. The reboiler 2 heats the bottom liquid that has been drawn out through the extracting pipe 8, and feeds the heated liquid back to the bottom of the reactive distillation column 1 through the conduit 14. Namely, the reboiler 2 circulates the bottom liquid while heating so that the temperature decreases gradually from the bottom toward the top of the reactive distillation column 1. The extracting pipe 8 branches so that a portion of the bottom liquid is continuously drawn out as a residue from the reaction system.

The condenser 3 condenses the distillate of the reactive distillation column 1 into a liquid phase. The condenser 3 is connected to the top of the reactive distillation column 1 through the conduit 12, and connected to the pump 4 through an extracting pipe 9. The condenser 3 includes a regulating pipe 10 provided with a pressure regulating valve 11. The extracting pipe 9 branches so that a portion of the distillate is continuously removed from the reaction system.

The pump 4 refluxes the distillate to the reactive distillation column 1 at a predetermined reflux ratio. The pump 4 is connected to the condenser 3 through the extracting pipe 9, and connected to the top of the reactive distillation column 1 through a conduit 13.

When the aliphatic carbonate ester (a) is fed, the temperature of the reactant liquid in the second stage decreases. Therefore, the pressure regulating valve 11 usually applies pressure to the inside of the reactive distillation column 1 so as to increase the operation pressure. As a result, the temperature of the reactant liquid in the second stage after the feeding of the aliphatic carbonate ester (a) can be maintained at the temperature of the reactant liquid in the second stage before the feeding of the aliphatic carbonate ester (a). The regulating pipe 10 is connected to a pressure reducing device such as a vacuum pump, or a pressure regulator such as a pressure application device.

The transesterification of the aromatic carboxylate with the aliphatic carbonate ester and/or the aromatic.aliphatic carbonate ester is carried out under the presence of a catalyst. Examples of the catalyst are: mineral acids such as sulfuric acid; sulfonic acids such as paratoluenesulfonic acid; solid acids such as ion exchange resins and zeolite; base such as sodium hydroxide; metal alkoxide such as tetraisopropoxide titanate, and zirconium(IV) isopropoxide; Lewis acid such as aluminum chloride and titanium tetrachloride, and compounds producing Lewis acid; metal phenoxides such as lead phenoxide and phenoxytitanium; lead oxides; lead salts such as lead carbonate; metal acetylacetonate complex such as zirconium(IV) acetylacetonate, copper (II) bis(acetylacetonate), zinc(II) acetylacetonate and lithium acetylacetonate; organotin compounds such as dibutyltin oxide; titanium silicate; and metalsubstituted aluminum phosphate. However, the catalyst is not particularly limited to these compounds. Among the listed catalysts, weak acid and weak base are particularly preferred because they improve the selectivity of the aromatic carbonate ester.

When using a homogeneous catalyst, it is possible to continuously feed the catalyst to the reactive distillation column 1 by mixing the catalyst with either or both of the aromatic carboxylate and the aliphatic carbonate ester and/or the aromatic.aliphatic carbonate ester. Alternatively, it is possible to continuously feed the catalyst to the reactive distillation column 1 separately from these raw materials. The catalyst and the raw materials can be fed to the same stage or different stages of the reactive distillation column 1.

In the reactive distillation column 1, when the number of regions (stages) in which the catalyst is present is increased, the contact frequency of the reactant liquid and the catalyst increases, thereby achieving excellent reaction efficiency. It is therefore desirable to feed the catalyst to a stage as high as possible in the reactive distillation column 1. The catalyst needs to be separated and collected from the residue using a known method, for example, distillation. It is possible to feed the catalyst to the reactive distillation column 1 after dissolving it in an appropriate solvent.

When the homogeneous catalyst is used, the minimum catalyst concentration is 0.1 ppm, preferably 1 ppm, and more preferably 10 ppm, based on the total amount of aromatic carboxylate, aliphatic carbonate ester and aromatic.aliphatic carbonate ester. The maximum catalyst concentration up to which the catalyst dissolves in a saturated state in the reactant liquid in the reactive distillation column 1 is about 10 weight percent, preferably 5 weight percent, and more preferably 1 weight percent.

When the solid heterogeneous catalyst is used, it is necessary to keep the catalyst inside the reactive distillation column 1 and bring the reactant liquid into contact with the catalyst. When a packed column (to be described later) is used as the reactive distillation column 1, it is possible to entirely or partially replace the material packed in the reactive distillation column 1 with the heterogeneous catalyst, i.e., pack the reactive distillation column 1 with the heterogeneous catalyst. When a plate column (to be described later) is used as the reactive distillation column 1, the heterogeneous catalyst can be retained on the plate or in the downcomer.

Factors determining the operating conditions of the reactive distillation column 1 are, for example, the number of stages, the operation temperature (reaction temperature), the operation pressure, the residence time of liquid, the reflux ratio, and the amount of hold-up liquid.

More specifically, the operation temperature varies depending on the kinds and combination of the raw material and aliphatic carbonate ester (a), the kind and amount of the catalyst and other conditions (factors). However, the temperature at the bottom of the reactive distillation column 1 is preferably not more than 300° C., and more preferably not more than 280° C. An operation temperature higher than 300° C. is not preferred because a side reaction is likely to occur, and the pressure inside the reactive distillation column 1 increases excessively.

The amount of hold-up liquid and the number of stages are closely related to the reaction time, i.e., the residence time. Namely, in order to improve the equilibrium conversion, it is necessary to increase the residence time to a certain extent. Moreover, in order to increase the residence time, it is necessary to increase the amount of hold-up liquid or the number of stages.

Although an increase in the amount of hold-up liquid is preferred, if the amount of hold-up liquid becomes larger than a certain value, flooding occurs. Therefore, the amount of hold-up liquid with respect to the capacity (volume) of an empty column of the reactive distillation column 1, i.e., the volume ratio of the hold-up liquid to the empty column, is preferably in a range of from 0.005 to 0.75, and more preferably in a range of from 0.01 to 0.5. In the case where the number of stages is increased, a preferred number of stages is approximately 2 to 100 stages considering the manufacturing cost of the reactive distillation column 1, the height restriction, and the costs of utility and installation, etc. When the number of stages is increased, the efficiency of vapor-liquid separation is improved.

The reflux ratio is preferably in a range of from 0 to 100, more preferably in a range of from 0 to 50, and still more preferably in a range of from 0 to 25. When one component of the raw material and the aliphatic carboxylate form an azeotrope, it is preferred to make the reflux ratio zero or a relatively small value. When the difference in boiling point between the one component and the aliphatic carboxylate is relatively small, it is preferred to make the reflux ratio a relatively large value considering the costs of utility, installation, etc.

When a heterogeneous catalyst is used, if the catalyst is retained in the reactive distillation column 1, it is not necessary to separate the catalyst. In this case, even when the catalyst is used in the form of slurry; the heterogeneous catalyst can be easily removed and collected from the residue after the completion of the reaction by employing a known method, for example, a centrifugal method or filtration.

On the other hand, when a homogeneous catalyst is used, the homogeneous catalyst can be easily separated and collected from the residue after the completion of the reaction by using a known method, for example, distillation. By separating the catalyst after the completion of the reaction using the above-mentioned method and using a known method such as distillation, extraction and recrystallization, the aromatic carbonate ester as a target product can be easily isolated.

Moreover, the aliphatic carboxylate as a by-product, or the aromatic carboxylate and the aliphatic carbonate ester and/or aromatic.aliphatic carbonate ester, etc. as unreacted compounds can be easily separated and collected, if necessary.

Next, the following description will explain an example of the process for preparing an aromatic carbonate ester using the reactive distillation column 1. First, the raw material and catalyst are continuously fed to the reactive distillation column 1 through the raw material feeding pipe 5, and the aliphatic carbonate ester (a) is continuously fed to the reactive distillation column 1 through the aliphatic carbonate ester feeding pipe 6. The raw material and the aliphatic carbonate ester (a) may be fed in liquid phase, gaseous phase, or vapor-liquid-mixed phase. In addition, the operation pressure of the reactive distillation column 1 is regulated by the pressure regulating valve 11, if necessary.

Reactive distillation is carried out by performing vapor-liquid contacting of the raw material fed to the reactive distillation column 1 under the presence of a catalyst. As a result, the equilibrium reaction proceeds, and an aromatic carbonate ester and an aliphatic carboxylate are produced and then separated from each other. The aromatic carbonate ester as the target product flows downward in the reactive distillation column 1, and is extracted continuously as a residue (bottom liquid). Namely, the aromatic carbonate ester is continuously extracted as the residue from the reaction system.

The aliphatic carboxylate as a by-product is continuously removed as a distillate from the reaction system. By performing the above-mentioned reaction, it is possible to improve the reaction efficiency of the transesterification, and produce the aromatic carbonate ester continuously and efficiently.

The reactive distillation equipment is not necessarily limited to the structure shown in FIG. 1. For example, the reactive distillation equipment can have two raw material feeding pipes so that the aromatic carboxylate, and the aliphatic carbonate ester and/or aromatic.aliphatic carbonate ester are continuously and separately fed to the reactive distillation column. Namely, the aromatic carboxylate, and the aliphatic carbonate ester and/or aromatic.aliphatic carbonate ester may be fed separately to different stages by connecting the two raw material feeding pipes to the different stages.

In this case, the aromatic carboxylate may contain a portion of the aliphatic carbonate ester and/or aromatic.aliphatic carbonate ester, and the aliphatic carbonate ester and/or aromatic.aliphatic carbonate ester may contain a portion of the aromatic carboxylate. However, in order to smoothly proceed the contacting of these compounds in the reactive distillation column, it is preferred to feed a raw material of a higher boiling point to a stage higher than a stage to which a raw material of a lower boiling point is fed.

As described above, the process for preparing aromatic carbonate esters of the present invention uses the reactive distillation column 1, and feeds the raw material continuously to the first stage while feeding the aliphatic carbonate ester (a) whose boiling point is lower than that of the reactant liquid in the second stage continuously to the second stage lower than the first stage.

In this method, since the aliphatic carbonate ester (a) is fed continuously, the reaction efficiency of the transesterification is improved. It is therefore possible to continuously and efficiently prepare aromatic carbonate esters.

In addition, as described above, a process for preparing aromatic carbonate esters of the present invention is a method in which the second stage is a column bottom section of the reactive distillation column 1. Moreover, as described above, a process for preparing aromatic carbonate esters of the present invention is a method in which the amount of the aliphatic carbonate ester (a) fed is 0.001 to 5 times, by weight, more than the amount of the raw material fed.

According to the above-mentioned methods, it is possible to continuously and more efficiently prepare aromatic carbonate esters.

The following description will explain in detail the present invention by presenting examples and comparative examples which should not be considered as limiting, in any way, the scope of the invention.

[EXAMPLE 1]

An aromatic carbonate ester was continuously prepared using a reactive distillation equipment shown in FIG. 1. In this case, a column formed by connecting a stainless distillation column to the top of a stainless packed column of an inner diameter of 55 mm was used as the reactive distillation column 1. The following description will briefly explain the packed column of the reactive distillation column 1 used in this example.

Figure 2:
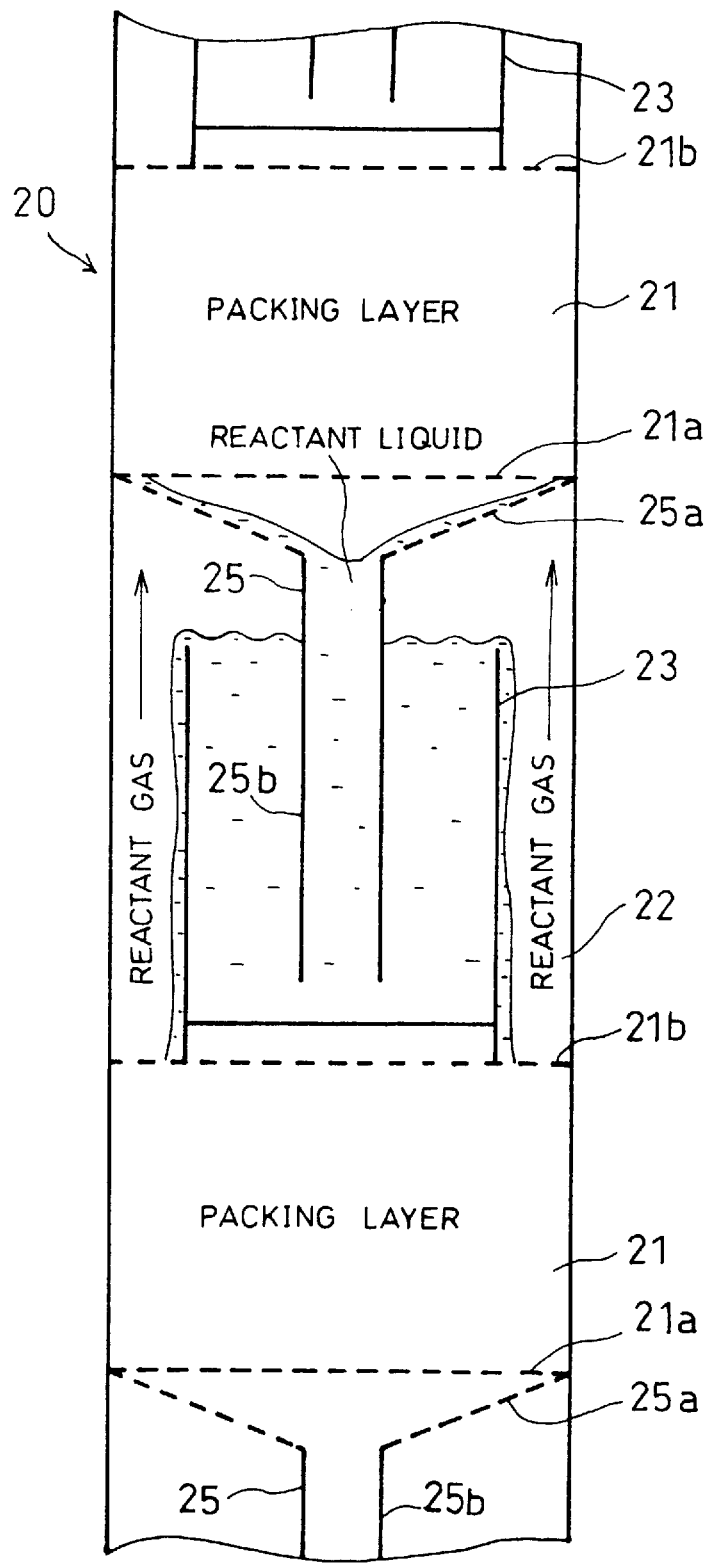
FIG. 2 is a cross section of essential sections, showing a schematic structure of a packed column of a reactive distillation equipment used in an embodiment of the present invention.

As illustrated in FIG. 2, the above-mentioned packed column 20 includes therein a packing layer 21, a rising section 22, a reservoir section 23, etc. The packing layer 21 is formed by packing a porous plate 21a that allows the passage of a reactant gas with a 3 mmφ stainless Dixon packing (not shown) as a packing material. Additionally, placed on the packing material is a porous plate 21b that allows the passage of a reactant gas. The packing layer 21 causes vapor-liquid contacting of the reactant liquid flowing downward in the column with the reactant gas moving upward in the column.

Provided below the packing layer 21 is a collector 25 including a funnel section 25a in the form of a funnel and a leg section 25b in the form of a tube. The funnel section 25a is made of a stainless wire netting. The leg section 25b is inserted into the reservoir section 23 so that the reactant liquid collected in the funnel section 25a is guided to the reservoir section 23.

As to the position of the rising section 22, the rising section is above the packing layer 21 (the lower packing layer in FIG. 2), and in the peripheral area with reference to the horizontal cross section of the reactive distillation column 1. The rising section 22 causes the reactant gas to move upward without making substantial vapor-liquid contacting.

The reservoir section 23 has a cylindrical shape with a base, and a capacity of 25 ml. The reservoir section 23 is positioned above the packing layer 21 (the lower packing layer in FIG. 2), and in the central area with reference to the horizontal cross section of the reactive distillation column 1. The reservoir section 23 stores the reactant liquid flowing downward through the collector 25 from the packing layer 21 (the upper packing layer in FIG. 2) located above the reservoir section 23. The reservoir section 23 allows a reaction of the raw material in the reactant liquid under the presence of a catalyst without making substantial vapor-liquid contacting.

When the amount of the reactant liquid stored in the reservoir section 23 becomes 25 ml or more, the reactant liquid overflows the reservoir section 23, and the overflowing reactant liquid flows downward along the external wall of the reservoir section 23 in the reactive distillation column 1 and is fed to the packing layer 21 in the lower stage.

In the packed column 20 of the above-mentioned structure, the packing layer 21, reservoir section 23 and rising section 22 form a unit, and this unit is piled up in five layers. The raw material feeding pipe 5 is connected to the packed column 20 above the fifth stage, and the aliphatic carbonate ester (a) feeding pipe 6 is connected below the first stage (the lowest plate), i.e., to the bottom of the column 20. Thus, the packed column 20 functions as a reactor section.

The above-mentioned distillation column had a height of 80 cm and an inner diameter of 20 mm, and was packed with a 3 mmφ stainless Dixon packing as a packing material. Hence, the distillation column serves as a condenser section.

Heat necessary for distillation was fed by heating the bottom of the packed column 20 with a heater instead of heating the bottom liquid using, for example, the reboiler 2. The operating conditions of the reactive distillation column 1 were a column bottom temperature of 230° C., and a column top pressure as an operation pressure of 58.7 kPa (440 Torr). The reflux ratio was made 0.41 by controlling the reflux amount per hour to be 30 grams.

A raw material liquid composed of the raw material and titanium tetraphenoxide "Ti(OPh)$_4$" as the catalyst was continuously fed to the reactive distillation column 1 through the raw material feeding pipe 5. The amount of the raw material liquid fed per hour was 119.9 grams. The composition of the raw material was 31.2 percent by weight of phenyl valerate (aromatic carboxylate), 21.6 percent by weight of methyl phenyl carbonate (aromatic.aliphatic carbonate ester), 10.9 percent by weight of dimethyl carbonate (aliphatic carbonate ester), 26.6 percent by weight of methyl valerate, 1.6 percent by weight of phenol, and 8.2 percent by weight of diphenyl carbonate as a target product. The titanium tetraphenoxide was added so that the amount of titanium was 400 ppm based on the amount of the raw material (all the components).

Dimethyl carbonate as the aliphatic carbonate ester (a) (whose boiling point at 1 atmospheric pressure (760 Torr) was 90.2° C.) was continuously fed in gaseous phase to the reactive distillation column 1 through the aliphatic carbonate ester (a) feeding pipe 6.

More specifically, in the stage of the reactive distillation column 1 to which the aliphatic carbonate ester (a) feeding pipe 6 is connected, the temperature and pressure are regulated so that most portions of dimethyl carbonate is maintained in a gaseous phase and the reactant liquid is retained in a liquid phase. The amount of dimethyl carbonate fed per hour is 11.5 grams. The above-mentioned reaction conditions, i.e., the flow and composition of the raw material and aliphatic carbonate ester (a) are shown in Table 1.

Vapor-liquid contacting was carried out while performing transesterification between the phenyl valerate and the methyl phenyl carbonate and dimethyl carbonate by manipulating the reactive distillation column 1 under the above-mentioned operation conditions. Then, the distillate containing the produced methyl valerate as a by-product was continuously removed from the reaction system through the extracting pipe 9. The amount of the distillate drawn out per hour was 72.7 grams. Meanwhile, the residue containing the diphenyl carbonate produced was continuously extracted from the reaction system through the extracting pipe 8. The amount of the residue drawn out per hour was 58.7 grams. The column top pressure, reflux ratio, etc. are shown in Table 2.

[TABLE 1]

|  | Raw material liquid | | Aliphatic carbonate ester (a) | |
|---|---|---|---|---|
|  | Flow (g/hr) | Composition (weight %) | Catalyst (ppm) | Flow (g/hr) | Composition (weight %) |
| Example 1 | 119.9 | phenyl valerate 31.2 methyl phenyl carbonate | Ti (OPh)₄ 400 | 11.5 | dimethyl carbonate 100.0 |

[TABLE 1]-continued

|  | Raw material liquid | | Aliphatic carbonate ester (a) | |
|---|---|---|---|---|
|  | Flow (g/hr) | Composition (weight %) | Catalyst (ppm) | Flow (g/hr) | Composition (weight %) |
|  |  | 21.6 dimethyl carbonate 10.9 methyl valerate 26.6 phenol 1.6 diphenyl carbonate 8.2 |  |  |  |
| Example 2 | 117.8 | Same as above | Same as above | 34.9 | Same as above |
| Comparative Example 1 | 120.0 | Same as above | Same as above | 0 | — |
| Example 3 | 122.7 | phenyl valerate 25.3 methyl phenyl carbonate 17.7 dimethyl carbonate 5.9 methyl valerate 16.6 phenol 25.1 diphenyl carbonate 9.5 | Ti (OPh)₄ 458 | 15.4 | dimethyl carbonate 100.0 |
| Comparative Example 2 | 122.8 | Same as above | Same as above | 0 | — |

[TABLE 2]

|  | Column top pressure (kPa) | Reflux ratio | Column bottom temperature (°C.) |
|---|---|---|---|
| Example 1 | 58.7 | 0.41 | 230 |
| Example 2 | 66.7 | 0.31 | 231 |
| Comparative Example 1 | 46.7 | 0.52 | 230 |
| Example 3 | 60.0 | 0.34 | 230 |
| Comparative Example 2 | 46.7 | 0.43 | 231 |

[TABLE 3]

|  | Distillate | | Residue | | Reaction Results | |
|---|---|---|---|---|---|---|
|  | Flow (g/hr) | Composition (wt. %) | Flow (g/hr) | Composition (wt. %) | Conversion of phenyl valerate (mol. %) | Conversion of dimethyl carbonate (mol. %) |
| Example 1 | 72.7 | methyl valerate 68.8 | 58.7 | diphenyl carbonate 71.9 phenyl valerate | 69.7 | 14.9 |

[TABLE 3]-continued

| | Distillate | | Residue | | Reaction Results | |
|---|---|---|---|---|---|---|
| | Flow (g/hr) | Composition (wt. %) | Flow (g/hr) | Composition (wt. %) | Conversion of phenyl valerate (mol. %) | Conversion of dimethyl carbonate (mol. %) |
| | | dimethyl carbonate 31.2 | | 19.3 methyl phenyl carbonate 6.4 methyl valerate 0.5 dimethyl carbonate 0.3 phenol 1.6 | | |
| Example 2 | 96.6 | methyl valerate 53.0 dimethyl carbonate 47.0 | 56.1 | diphenyl carbonate 70.0 phenyl valerate 18.6 methyl phenyl carbonate 8.5 methyl valerate 0.4 dimethyl carbonate 0.6 phenol 1.8 | 71.6 | 5.7 |
| Comparative Example 1 | 57.9 | methyl valerate 73.1 dimethyl carbonate 26.9 | 62.1 | diphenyl carbonate 61.4 phenyl valerate 31.9 methyl phenyl carbonate 4.5 methyl valerate 0.6 phenol 1.6 | 47.1 | — |

[TABLE 4]

| | Distillate | | Residue | | Reaction Results | |
|---|---|---|---|---|---|---|
| | Flow (g/hr) | Composition (wt. %) | Flow (g/hr) | Composition (wt. %) | Conversion of phenyl valerate (mol. %) | Conversion of dimethyl carbonate (mol. %) |
| Example 3 | 87.5 | methyl valerate 40.5 dimethyl carbonate 25.0 phenol 34.5 | 50.6 | diphenyl carbonate 74.6 phenyl valerate 15.1 methyl phenyl carbonate 7.7 methyl valerate 0.4 dimethyl carbonate 0.4 phenol 1.9 | 75.4 | 3.6 |
| Comparative Example 2 | 69.6 | methyl valerate 41.9 dimethyl carbonate 13.8 phenol 44.3 | 53.7 | diphenyl carbonate 62.6 phenyl valerate 31.0 methyl phenyl carbonate 4.3 phenol 2.2 | 46.4 | — |

The composition of the distillate was analyzed. The distillate contained 68.8 percent by weight of methyl valerate, and 31.2 percent by weight of dimethyl carbonate. The composition of the residue was analyzed. The residue contained 71.9 percent by weight of diphenyl carbonate, 19.3 percent by weight of phenyl valerate, 6.4 percent by weight of methyl phenyl carbonate, 0.5 percent by weight of methyl valerate, 0.3 percent by weight of dimethyl carbonate, and 1.6 percent by weight of phenol. Thus, the conversion of phenyl valerate was 69.7 mole percent, and the conversion of dimethyl carbonate was 14.9 mole percent. The flow and composition of the distillate and residue, and the results of the reaction are shown in Table 3. The conversion of the dimethyl carbonate is given by dividing a converted amount of dimethyl carbonate by an amount of dimethyl carbonate fed as the aliphatic carbonate ester (a) and expressing the obtained value in percentage.

[EXAMPLE 2]

Transesterification was carried out using the same reactive distillation equipment as that used in Example 1 under the same reaction conditions as those in Example 1, except that the amount of the raw material liquid fed per hour was changed to 117.8 grams from 119.9 grams of Example 1, the amount of the aliphatic carbonate ester (a) fed per hour was changed to 34.9 grams from 11.5 grams, the column top pressure was changed to 66.7 kPa (500 Torr) from 58.7 kPa (440 Torr), and the reflux ratio was changed to 0.31 from 0.41. The above-mentioned reaction conditions, i.e., the flow and compositions of the raw material liquid and aliphatic carbonate ester (a) are shown in Table 1.

A distillate containing methyl valerate as a by-product was continuously removed from the reaction system. The amount of the distillate removed per hour was 96.6 grams. Meanwhile, a residue containing diphenyl carbonate produced was continuously extracted from the reaction system. The amount of the residue removed per hour was 56.1 grams. The column top pressure, reflux ratio, etc. are shown in Table 2.

The composition of the distillate was analyzed. The distillate contained 53.0 percent by weight of methyl valerate, and 47.0 percent by weight of dimethyl carbonate. The composition of the residue was analyzed. The residue contained 70.0 percent by weight of diphenyl carbonate, 18.6 percent by weight of phenyl valerate, 8.5 percent by weight of methyl phenyl carbonate, 0.4 percent by weight of methyl valerate, 0.6 percent by weight of dimethyl carbonate, and 1.8 percent by weight of phenol. The conversion of phenyl valerate was 71.6 mole percent, and the conversion of dimethyl carbonate was 5.7 mole percent. The flow and composition of the distillate and residue, and the results of the reaction are shown in Table 3.

[COMPARATIVE EXAMPLE 1]

Transesterification was carried out using the same reactive distillation equipment as that used in Example 1 under the same reaction conditions as those in Example 1, except that the amount of the raw material liquid fed per hour was changed to 120.0 grams from 119.9 grams of Example 1, the amount of the aliphatic carbonate ester (a) fed per hour was changed to 0 gram from 11.5 grams, the column top pressure was changed to 46.7 kPa (350 Torr) from 58.7 kPa (440 Torr), and the reflux ratio was changed to 0.52 from 0.41. In short, a comparative transesterification reaction was performed without using the aliphatic carbonate ester (a). The above-mentioned reaction conditions, i.e., the flow and compositions of the raw material and aliphatic carbonate ester (a) are shown in Table 1.

A distillate containing methyl valerate as a by-product was continuously removed from the reaction system. The amount of the distillate removed per hour was 57.9 grams. Meanwhile, a residue containing diphenyl carbonate produced was continuously extracted from the reaction system. The amount of the residue removed per hour was 62.1 grams. The column top pressure, reflux ratio, etc. are shown in Table 2.

The composition of the distillate was analyzed. The distillate contained 73.1 percent by weight of methyl valerate, and 26.9 percent by weight of dimethyl carbonate. The composition of the residue was analyzed. The residue contained 61.4 percent by weight of diphenyl carbonate, 31.9 percent by weight of phenyl valerate, 4.5 percent by weight of methyl phenyl carbonate, 0.6 percent by weight of methyl valerate, and 1.6 percent by weight of phenol. The conversion of phenyl valerate was as low as 47.1 mole percent. The flow and composition of the distillate and residue, and the results of the reaction are shown in Table 3.

[EXAMPLE 3]

Aromatic carbonate ester was continuously prepared using the same reactive distillation equipment as that used in Example 1. However, the operation conditions of the reactive distillation column 1 were changed so that the column bottom temperature was 230° C., the column top pressure was 60.0 kPa (450 Torr), and the reflux ratio was 0.34.

A raw material liquid composed of the raw material and titanium tetraphenoxide was continuously fed to the reactive distillation column 1 through the raw material feeding pipe 5. The amount of raw material liquid fed per hour was 122.7 grams. The composition of the raw material was 25.3 percent by weight of phenyl valerate, 17.7 percent by weight of methyl phenyl carbonate, 5.9 percent by weight of dimethyl carbonate, 16.6 percent by weight of methyl valerate, 25.1 percent by weight of phenol, and 9.5 percent by weight of diphenyl carbonate. The titanium tetraphenoxide was added so that the amount of titanium was 458 ppm based on the amount of the raw material (all the components)

Dimethyl carbonate was continuously fed in gaseous phase to the reactive distillation column 1 through the aliphatic carbonate ester (a) feeding pipe 6. The amount of dimethyl carbonate fed per hour was 15.4 grams. The above-mentioned reaction conditions, i.e., the flow and composition of the raw material liquid and aliphatic carbonate ester (a) are shown in Table 1.

Vapor-liquid contacting was carried out by manipulating the reactive distillation column 1 under the above-mentioned operation conditions while performing transesterification of the phenyl valerate with the methyl phenyl carbonate and dimethyl carbonate. Then, a distillate containing methyl valerate as a by-product was continuously removed from the reaction system. The amount of the distillate drawn out per hour was 87.5 grams. Meanwhile, a residue containing diphenyl carbonate produced was continuously extracted from the reaction system. The amount of the residue drawn out per hour was 50.6 grams. The column top pressure, reflux ratio, etc. are shown in Table 2.

The composition of the distillate was analyzed. The distillate contained 40.5 percent by weight of methyl valerate, 25.0 percent by weight of dimethyl carbonate, and 34.5 percent by weight of phenol. The composition of the residue was analyzed. The residue contained 74.6 percent by weight of diphenyl carbonate, 15.1 percent by weight of phenyl valerate, 7.7 percent by weight of methyl phenyl carbonate, 0.4 percent by weight of methyl valerate, 0.4 percent by weight of dimethyl carbonate, and 1.9 percent by weight of phenol. Thus, the conversion of phenyl valerate was 75.4 mole percent, and the conversion of dimethyl carbonate was 3.6 mole percent. The flow and composition of each of the distillate and residue, and the results of the reaction are shown in Table 4.

[COMPARATIVE EXAMPLE 2]

Transesterification was carried out using the same reactive distillation equipment as that used in Example 1 under the same reaction conditions as those in Example 3, except that the amount of the raw material liquid fed per hour was changed to 122.8 grams from 122.7 grams of Example 3, the amount of the aliphatic carbonate ester (a) fed per hour was changed to 0 gram from 15.4 grams, the column top pressure was changed to 46.7 kPa (350 Torr) from 60.0 kPa (450 Torr), and the reflux ratio was changed to 0.43 from 0.34. In short, a comparative transesterification reaction was performed without using the aliphatic carbonate ester (a). The above-mentioned reaction conditions, i.e., the flow and compositions of the raw material liquid and aliphatic carbonate ester (a) are shown in Table 1.

A distillate containing methyl valerate as a by-product was continuously removed from the reaction system. The amount of the distillate removed per hour was 69.6 grams. Meanwhile, a residue containing diphenyl carbonate produced was continuously extracted from the reaction system. The amount of the residue removed per hour was 53.7 grams. The column top pressure, reflux ratio, etc. are shown in Table 2.

The composition of the distillate was analyzed. The distillate contained 41.9 percent by weight of methyl valerate, 13.8 percent by weight of dimethyl carbonate, and 44.3 percent by weight of phenol. The composition of the residue was analyzed. The residue contained 62.6 percent by weight of diphenyl carbonate, 31.0 percent by weight of phenyl valerate, 4.3 percent by weight of methyl phenyl carbonate, and 2.2 percent by weight of phenol. Thus, the conversion of phenyl valerate was as low as 46.4 mole percent. The flow and composition of each of the distillate and residue, and the results of the reaction are shown in Table 4.

It is considered that, when dimethyl carbonate is fed to the reactive distillation column 1 from the bottom of the column 1, a portion of the dimethyl carbonate causes disproportionation (an equilibrium reaction) with diphenyl carbonate as a target product, and produces methyl phenyl carbonate. Namely, there is a possibility that the feeding of dimethyl carbonate from the bottom of the reactive distillation column 1 interferes with the production of diphenyl carbonate.

However, it is clear from the results of Examples 1 to 3 and Comparative Examples 1 and 2 that the present embodiment improves the conversion of phenyl valerate and increases the yield of diphenyl carbonate. Thus, the preparation process according to the present embodiment produces an excellent effect of improving the reaction efficiency.

Namely, as is clear from the results of Examples 1 to 3 and Comparative Examples 1 and 2, the reaction efficiency (equilibrium conversion) can be improved by adopting the preparation process according to the present embodiment. It is thus possible to continuously and efficiently prepare diphenyl carbonates as aromatic carbonate esters.

INDUSTRIAL APPLICABILITY

Since a process for preparing aromatic carbonate esters of the present invention can improve the reaction efficiency of the transesterification in preparing aromatic carbonate esters, it is possible to prepare industrially useful aromatic carbonate esters continuously and efficiently.

We claim:

1. A process for preparing an aromatic carbonate ester by performing transesterification of an aromatic carboxylate with an aliphatic carbonate ester and/or an aromatic.aliphatic carbonate ester, using multistage reactive distillation equipment having a first stage and a second stage lower than said first stage, said process comprising the step of feeding a raw material that includes said aromatic carboxylate and said aliphatic carbonate ester and/or aromatic.aliphatic carbonate ester continuously to said first stage while feeding an aliphatic carbonate ester whose boiling point is lower than a boiling point of a reactant liquid that is present in said second stage continuously to said second stage.

2. The process for preparing an aromatic carbonate ester as set forth in claim 1, wherein said second stage is a column bottom section of said reactive distillation equipment.

3. The process for preparing an aromatic carbonate ester as set forth in claim 1, wherein the amount of said aliphatic carbonate ester fed to said second stage is 0.001 to 5 times, by weight, more than the amount of said raw material fed.

4. The process for preparing an aromatic carbonate ester as set forth in claim 1, wherein said aromatic carboxylate has a boiling point higher than the boiling point of the aliphatic carboxylate as a by-product of the transesterification.

5. The process for preparing an aromatic carbonate ester as set forth in claim 1, wherein said aromatic carboxylate, said aliphatic carbonate ester, and/or said aromatic.aliphatic carbonate ester have boiling points lower than the boiling point of said aromatic carbonate ester.

6. The process for preparing an aromatic carbonate ester as set forth in claim 4, wherein the difference in boiling point between said aromatic carbonate ester and said aliphatic carboxylate is greater than the difference in boiling point between said aromatic carboxylate, and said aliphatic carbonate ester and/or said aromatic.aliphatic carbonate ester.

7. The process for preparing an aromatic carbonate ester as set forth in claim 1, wherein said aliphatic carbonate ester to be fed to said second stage is fed in a gaseous phase.

8. The process for preparing an aromatic carbonate ester as set forth in claim 1, wherein a temperature and the pressure in said second stage are controlled to exceed the boiling point of said aliphatic carbonate ester fed to said second stage and to be lower than a boiling point of said reactant liquid in said second stage.

* * * * *